United States Patent
Ali et al.

(10) Patent No.: US 8,034,280 B2
(45) Date of Patent: Oct. 11, 2011

(54) BALLOON CATHETERS AND METHODS FOR MANUFACTURING BALLOONS FOR BALLOON CATHETERS

(75) Inventors: Afsar Ali, Maple Grove, MN (US); Daniel J. Horn, Shoreview, MN (US); Jan Weber, Maastricht (NL); Scott Schewe, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/552,223

(22) Filed: Sep. 1, 2009

(65) Prior Publication Data
US 2009/0318862 A1 Dec. 24, 2009

Related U.S. Application Data

(63) Continuation of application No. 10/819,469, filed on Apr. 7, 2004, now abandoned.

(51) Int. Cl.
*B29C 55/00* (2006.01)
*H05B 6/00* (2006.01)
*B29C 39/02* (2006.01)
*D02J 1/06* (2006.01)
*A61M 29/00* (2006.01)
*A61M 29/02* (2006.01)

(52) U.S. Cl. ........ 264/479; 264/454; 264/458; 264/481; 264/482; 264/167; 264/523; 264/288.4; 264/288.8; 604/96.01; 604/103.06

(58) Field of Classification Search .............. None
See application file for complete search history.

(56) References Cited

U.S. PATENT DOCUMENTS

| | | | |
|---|---|---|---|
| 3,141,912 A | 7/1964 | Goldman et al. |
| 3,304,353 A | 2/1967 | Harautuneian |
| 4,002,709 A | 1/1977 | Mozer |
| 4,007,243 A | 2/1977 | Rupert |
| 4,439,394 A | 3/1984 | Appleyard |

(Continued)

FOREIGN PATENT DOCUMENTS
EP 0318919 6/1989
(Continued)

OTHER PUBLICATIONS

ATLAS Confidence Redefined, Large Diameter PTA Dilatation Catheter, Bard Peripheral Vascular product brochure, 4 pages.

(Continued)

*Primary Examiner* — Jeffrey Wollschlager
(74) *Attorney, Agent, or Firm* — Seager, Tufte & Wickhem, LLC (57) ABSTRACT

Catheters, balloons, and methods of manufacturing balloons for balloon catheters using lasers are disclosed. A catheter with a shaft sized for use with a 0.014 inch guide wire includes a polymeric balloon having a body portion with an inflated outer diameter of more than 6 millimeters. An inflatable balloon includes an inflated outer diameter to inner waist diameter ratio of 12.5 to 1. An inflatable polymeric balloon that has a body portion with two regions that have different molecular orientations is also provided. A method of processing an elongate polymeric material includes heating a portion of the polymeric material with a laser while longitudinally stretching the portion of the polymeric material. A method of manufacturing a balloon includes heating and longitudinally stretching a first and second portion of an elongate polymeric tube to form first and second end portion. The remaining body portion is radially expanded to form the balloon.

15 Claims, 6 Drawing Sheets

U.S. PATENT DOCUMENTS

| | | | |
|---|---|---|---|
| 4,490,421 A | 12/1984 | Levy | |
| 4,963,306 A | 10/1990 | Weldon | |
| 4,963,313 A | 10/1990 | Noddin et al. | |
| 5,017,325 A | 5/1991 | Jackowski et al. | |
| 5,087,394 A | 2/1992 | Keith | |
| 5,100,379 A * | 3/1992 | Wendell | 604/512 |
| 5,223,205 A | 6/1993 | Jackowski et al. | |
| 5,248,471 A | 9/1993 | Kavesh | |
| 5,304,340 A | 4/1994 | Downey | |
| 5,449,371 A | 9/1995 | Pinchuk et al. | |
| 5,500,180 A | 3/1996 | Anderson et al. | |
| 5,501,759 A | 3/1996 | Forman | |
| 5,522,961 A | 6/1996 | Leonhardt | |
| 5,556,383 A | 9/1996 | Wang et al. | |
| 5,587,125 A | 12/1996 | Roychowdhury | |
| 5,714,110 A | 2/1998 | Wang et al. | |
| 5,746,968 A | 5/1998 | Radisch, Jr. | |
| 5,792,415 A | 8/1998 | Hijlkema | |
| 5,807,520 A | 9/1998 | Wang et al. | |
| 5,891,386 A | 4/1999 | Deitermann et al. | |
| 5,948,345 A | 9/1999 | Patel et al. | |
| 6,024,722 A | 2/2000 | Rau et al. | |
| 6,051,175 A | 4/2000 | Kurihara et al. | |
| 6,110,142 A | 8/2000 | Pinchuk et al. | |
| 6,132,824 A | 10/2000 | Hamlin | |
| 6,136,258 A | 10/2000 | Wang et al. | |
| 6,168,748 B1 | 1/2001 | Wang et al. | |
| 6,420,649 B1 | 7/2002 | Kahl et al. | |
| 6,482,348 B1 | 11/2002 | Wang et al. | |
| 6,488,654 B2 | 12/2002 | Gonzalez et al. | |
| 6,495,090 B1 | 12/2002 | Wilkins | |
| 6,537,480 B1 | 3/2003 | Becker et al. | |
| 6,572,813 B1 | 6/2003 | Zhang et al. | |
| 6,592,703 B1 | 7/2003 | Habeck et al. | |
| 6,599,462 B1 | 7/2003 | Miraki | |
| 6,645,422 B2 | 11/2003 | Jung, Jr. et al. | |
| 6,740,191 B2 | 5/2004 | Clarke et al. | |
| 6,818,728 B2 | 11/2004 | Kato et al. | |
| 6,905,572 B2 | 6/2005 | Yu | |
| 7,172,796 B2 | 2/2007 | Kinoshita et al. | |
| 2003/0015284 A1 | 1/2003 | Merdan et al. | |
| 2003/0201059 A1 | 10/2003 | Holman et al. | |

FOREIGN PATENT DOCUMENTS

| | | |
|---|---|---|
| WO | 9612516 | 5/1996 |
| WO | 03008009 | 1/2003 |
| WO | 03082545 | 10/2003 |
| WO | 03091005 | 11/2003 |

OTHER PUBLICATIONS

Bergman et al., "Impact of ultraviolet-laser heating on the photoluminescence of ensembles of GaN microcrystallites," Applied Physics Letters, 2003, 83(4): 764-766.

Bormashenko et al., "Infrared laser radiation induced changes in the IR absorption spectra of tin polymer films," J. Opt. A: Pure Appl. Opt., 2000, 2(5): L38-L40.

Examination Report in EP 05 732 477.4 mailed May 16, 2008, 7 pages.

Guidant product information, VIOTRAC 14 PLUS Peripheral Dilatation Catheter, printed from the internet on Aug. 24, 2004, http://www.guidant.com/products/ProductTemplates/ES/viatract_14_ifu.shtm.

Guidant product information AGILTRAC .018 Peripheral Dilatation Catheter, printed from internet on Aug. 24, 2004, http://www.guidant.com/products/ProductTemplates./ES/agiltrac018_ous_intro.shtml.

"Laser welding of polymers," Engineeringtalk, Dec. 22, 2003.

* cited by examiner

BALLOON CATHETERS AND METHODS FOR MANUFACTURING BALLOONS FOR BALLOON CATHETERS

CROSS-REFERENCE TO RELATED APPLICATION

This application is a continuation of U.S. application Ser. No. 10/819,469, filed Apr. 7, 2004, now abandoned, the entire disclosure of which is hereby incorporated by reference.

TECHNICAL FIELD

This invention relates to balloons for medical devices such as balloon catheters, and also to manufacturing such balloons using a heating and stretching process that uses laser energy for the heating.

BACKGROUND

Balloon catheters are used to perform various medical procedures within the body. One example is a percutaneous transluminal coronary angioplasty (PTCA). To perform a PTCA, a physician guides a balloon catheter through the vascular system over a guide wire until the catheter's balloon is positioned across a thrombus, commonly referred to as a lesion, that has reduced or completely blocked blood flow through a vessel. Once placed, the balloon is inflated radially, or that is, outwardly, to a pre-determined diameter, for example 9 millimeters, to reestablish blood flow through the vessel.

To maneuver a distal end of the balloon catheter through the vascular system to treat a lesion that has a very small opening requires the balloon catheter to have a small crossing profile, which is the largest cross-sectional diameter of the balloon portion of the balloon catheter. One portion of the crossing profile is the diameter of the catheter's shaft, which must be large enough to allow a guide wire to pass freely through a guide wire lumen in the shaft in a longitudinal direction. Catheters that use a guide wire with a larger diameter will have a larger catheter shaft and vice-versa. Existing catheters typically use guide wires that have cross-sectional diameters in the range of fourteen thousandths of an inch (0.014) up to 35 thousandths of an inch (0.035). Smaller guide wires make it easier to maneuver the balloon catheter through the body. Consequently, many doctors that perform cardiac procedures prefer using balloon catheters with a 0.014 inch guide wire.

Another portion of a balloon catheter's crossing profile is the thickness of the folded balloon, particularly at the balloon's folded cone and waist portions. Catheter balloons typically have a body portion near the center of the balloon, which is the portion of the balloon that expands. The balloon's waist portions are located at the balloon's proximal and distal ends, and the cone portions are located between the balloon's body portion and the waist portions. Typically, the wall thickness of the entire balloon is restricted to the dimensions of the original tubing material, or parison, from which the balloon is formed. Thus, an overall reduction in the wall thickness of the parison to reduce the thickness of the cone and waist portions will also result in a similar reduction of the wall thickness of the parison in the body portion. A reduced body portion wall thickness, however, limits the diameter to which the balloon may be inflated while maintaining a satisfactory hoop strength, which is a measure of a balloon's ability to withstand internal pressure. Consequently, there have been continuing efforts to form balloons made of materials suitable for cardiac procedures, such as Nylon 12, PEBAX, PET, and PEEK, that have large inflation diameters, for example 9 millimeters, and small crossing profiles.

One method of forming balloons with body portions that have a greater wall thickness and waist portions that have a reduced wall thickness is to physically remove, or grind away, the undesired thickness of the waist portions. This method may be performed, for example, by using a laser ablation process utilizing UV excimer lasers or ultrashort lasers. The physical removal of the wall, however, has not been able to produce a balloon that has an inflation diameter of greater than six millimeters for use on a catheter having a 0.014 inch guide wire.

The wall thickness of a polymer tube may also be changed by a stretching, or "drawing down," process. Using this process, the wall thickness of the tubing may be locally reduced in the cone and waist portions of the balloon. Heating is advantageous during the stretching process because polymers have certain thermophysical characteristics that cause them to soften and flow upon heating. Thus, with the use of heat, it is possible to target a specific portion of a polymer tube for stretching. Various heating methods are used to heat polymer tubes for stretching. These methods include passing a polymer tube through a heated ring and putting the tube in a hot oil or hot water bath. These methods, however, result in a large heating area and do not provide the ability to target small areas of the polymer tube for stretching. For example, the heating area of a heated ring is typically greater than five millimeters along the axial direction. The heating area of a hot oil or hot water bath is even greater. Thus, these methods that essentially provide heat from the outside of the tube are not suitable to vary the amount of stretching of a coronary balloon, which is typically one to two centimeters in length (the cone and waist portions being only a few millimeters in length). Moreover, it takes several seconds to change the amount of heat applied to the polymer tube using these methods.

SUMMARY

The invention features balloons, catheters, and methods of manufacturing balloons for balloon catheters using lasers. The use of lasers for heating allows small areas of a polymer tube to be targeted for stretching. Lasers also allow the heat to be delivered uniformly throughout the bulk of the polymer tube instead of relying on heat conductivity from the tube's outer layers. In addition, lasers provide the ability to instantaneously change the amount of heat applied during the process to precisely vary the amount of stretching in the various portions of the polymer tube.

The ability to instantaneously change the heat provided during stretching also allows the molecular orientation of the balloon to be varied throughout its length.

In one aspect, the invention features a method of manufacturing a balloon for a balloon catheter. The method includes heating and longitudinally stretching a first portion of an elongate polymer to form a first reduced diameter portion of the tube that serves as a first end portion for the balloon. A second portion of the tube is heated and longitudinally stretched to form a second reduced diameter portion of the tube that serves as a second end portion for the balloon that is opposite the first end portion. A body portion located between the first and second end portions is expanded radially to form the balloon.

In embodiments, the heating of the first and second portions may be performed by a laser, which may emit a beam in the infrared frequency range to heat the first and second portions. In some implementations, the elongate polymeric tube may have a uniform diameter before the method is performed.

The balloon may have an inflatable body portion with sufficient hoop strength for use in an angioplasty procedure. The inflated outer diameter of the balloon may be more than about six millimeters, for example, about 9 millimeters. In implementations where the first end portion of the balloon includes a first waist section and the second end portion of the balloon includes a second waist section, the first and second waist sections may have an inner diameter such that the balloon may be affixed to a catheter shaft that has an inner lumen sized appropriately to accommodate a guide wire having a diameter of at most about 0.014 inches. The first and second waist sections may have an inner diameter that is, for example, no more than 0.028 inches. In some implementations, the formed balloon may have an inflatable body portion that has a longitudinal length suitable for use in an angioplasty procedure. In other implementations, the inflatable body portion of the balloon may have a longitudinal length of no more than about 30 millimeters.

In another aspect, the invention also features a catheter that includes an elongate shaft having a lumen that extends longitudinally through the shaft. The lumen is sized appropriately to accommodate a guide wire having a diameter of at most about 0.014 inches. An inflatable polymeric balloon is affixed circumferentially about the shaft near the distal end of the shaft, and has an inflated outer diameter of more than about 6 millimeters.

In embodiments, the balloon may be formed by heating and longitudinally stretching a first portion of an elongate polymeric tube to form a first reduced diameter portion of the tube that serves as a first end portion for the balloon, and heating and longitudinally stretching a second portion of the tube to form a second reduced diameter portion of the tube that serves as a second end portion for the balloon that is opposite the first end portion. A body portion located between the first and second end portions may be expanded radially to form the balloon. In some implementations, before the balloon is formed, the elongate polymeric tube has a uniform diameter. The heating of the first and second portions may be performed by a laser, which may emit a beam in the infrared frequency range to heat the first and second portions.

In some embodiments, the balloon's body portion may have an inflated outer diameter of 9 millimeters and may be suitable for use in an angioplasty procedure. The balloon may have a first end portion that includes a first waist section and a second end portion that includes a second waist section. The first and second waist sections may have an inner diameter of no more than about 0.028 inches.

In another aspect, the invention features an inflatable polymeric balloon for a balloon catheter. The balloon includes a waist portion having an inner diameter that fits circumferentially around and is affixable to an elongate shaft that has an inner lumen sized appropriately to accommodate a guide wire having a diameter of at most about 0.014 inches. The balloon's body portion has an inflated outer diameter, the ratio of the outer diameter of the body portion to the inner diameter of the waist portion being at least 12.5 to 1.

In embodiments, the balloon may be formed by heating and longitudinally stretching a portion of an elongate polymeric tube. The polymeric tube from which the balloon is formed may have a uniform diameter before the heating and stretching. The heating of the tube may be performed by a laser, which may emit a beam in the infrared frequency range. In some embodiments, the inner diameter of the waist portion may be about 0.028 inches or less. The balloon may also have an inflated outer diameter of more than about 6 millimeters, for example, about 9 millimeters. Further, the balloon may have an inflatable body portion with sufficient hoop strength for use in an angioplasty procedure.

In another aspect, the invention features a method of processing an elongate polymeric material for use in a medical device that is placed inside a body. The method involves heating a portion of the polymeric material with a laser while longitudinally stretching the portion of the polymeric material.

In embodiments, the laser may emit a beam in the infrared frequency range to heat the polymeric material, which may be Nylon 12, PEBAX, PET, or PEEK. The laser may have a heating area of approximately two millimeters or less. The method may also include cooling the heated portion of the polymeric material after it has been longitudinally stretched to the desired dimension. A control system may be used to control the heating and stretching of the polymeric material.

In another aspect, the invention features an inflatable balloon for a balloon catheter constructed of a single polymeric material and having first and second regions. The polymeric material in the first section is oriented in a fashion that results from the balloon's body portion being stretched while being heated by a laser. The polymeric material in the second region is oriented differently from the first region.

In embodiments, the balloon may have an inflatable body portion that has a longitudinal length suitable for use in an angioplasty procedure. In other implementations, the balloon may have a longitudinal length of at most about 30 millimeters. The laser may emit a beam in the infrared frequency range to heat the polymeric material, which may be Nylon 12, PEBAX, PET, or PEEK.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
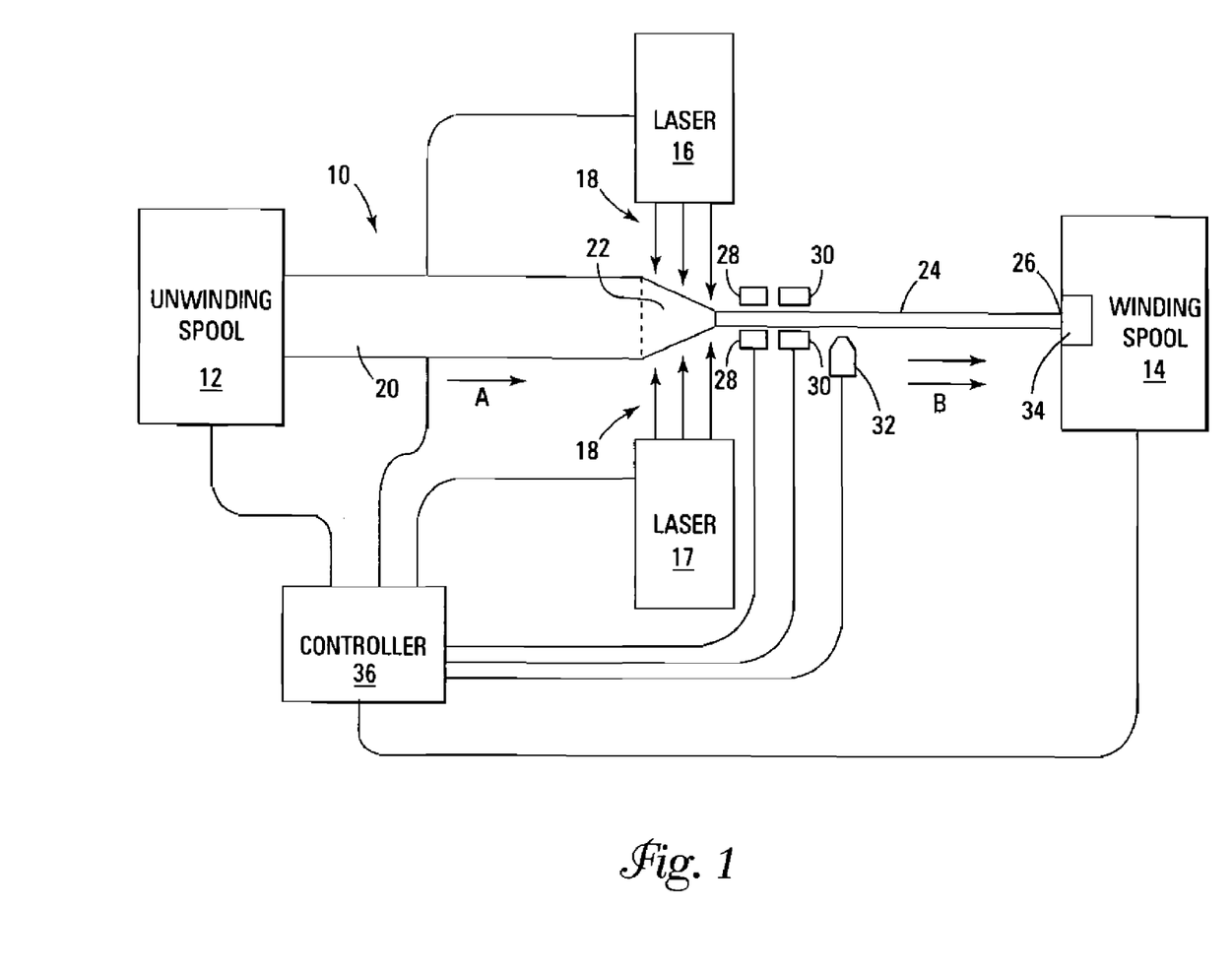
FIG. 1 is a diagram of an elongate polymer tube and a system for processing the elongate polymer tube.

FIG. 1 shows an elongate polymer tube 10 being processed to produce, for example, a balloon for a balloon catheter (not shown). In this example, the polymer tube 10 is being released from an unwinding spool and motion system 12 at a selected speed, as indicated by arrow A. At the same time, the polymer tube's leading end 26, which is secured to a winding spool system 14, is being pulled by the winding system 14.

Two laser devices 16 and 17 each direct a laser beam 18 toward a small target portion 22 of the polymer tube 10 to quickly heat the target portion 22 to a desired elevated temperature for stretching. The speed, indicated by double arrows B, at which the winding system 14 pulls the secured leading end 26 of the polymer tube 10 away from the unwinding spool 12 is selected to be greater than the speed at which the unwinding spool 12 is releasing the tube 10. Thus, the winding system 14 exerts a longitudinal pulling force on the polymer tube 10, thereby stretching the tube at the heated target portion 22 and reducing the cross-sectional diameter and wall thickness of the tube's target portion 22.

In this example, it will be appreciated that a leading portion 24 of the tube 10 located between the tube's leading end 26 and the target portion 22 has already been heated and stretched, whereas a trailing portion 20 of the tube 10 located between the tube's target portion 22 and the unwinding spool 12 has not yet been heated and stretched. Therefore, the leading portion 24 of the tube 10 is shown to have a smaller cross-sectional diameter than that of the tube's trailing portion 20.

A temperature sensor 28 is positioned to sense the temperature of the tube's target portion 22 as it is heated by lasers 16 and 17. An optical filter (not shown) may be placed between the temperature sensor 28 and the lasers 16 and 17 to eliminate reflection from the lasers 16 and 17 into the sensor 28. A diameter sensor 30 is positioned to sense the diameter of the tube 10 at a portion of the tube 10 that has most recently been stretched. In this example, the diameter sensor 30 senses the diameter at a portion of the tube's leading portion 24 that is near the target portion 22. The system also includes a tension sensor 34 to measure the tension in the tube 10 caused by the difference in the pulling speed of the winding system 14 and the speed at which the tube 10 is provided by the unwinding spool 12. A cooling device 32 is positioned to cool a heated and stretched portion of the tube's leading portion 24. The cooling of the heated portion of the tube 24 may prevent the tube 24 from stretching beyond a desired range as the longitudinal force continues to be applied to the tube 24 by the winding system 14 during the stretching process. The cooling device 32 may be placed distal to the sensors 28 and 30, as shown in FIG. 1, or alternatively, may be placed between the lasers 16 and 17 and the sensors 28 and 30.

A controller 36 is connected to the temperature sensor 28, the diameter sensor 30, and the tension sensor 34. The controller receives the temperature readings of the heated portion 22 of the tube 10 from the temperature sensor 28, cross-sectional diameter readings from the diameter sensor 30, and tension readings from the tension 34 sensor. The controller is also connected to the unwinding spool 12, the winding system 14, the lasers 16 and 17, and the cooling device 32 to control the operation of each. Thus, the entire processing of the polymer tube 10 to reduce the diameter of selected portions of the tube 10 may be under computer control with feedback.

In the FIG. 1 example, the laser devices 16 and 17 may be solid-state Yag lasers that emit laser beams 18 with an emission frequency in a range with a high enough absorption coefficient to cause adequate heating of the polymer tube 10. Frequency ranges may be in the far infrared, near infrared, visible range, and UV bands. In other implementations, the laser devices 16 and 17 may be a CO2 laser, a diode laser, or another suitable laser type. Alternatively, microwave generators emitting waves in the frequency bands from 2 GHz to 100 GHz may be used. Like laser heating, heating with microwaves offers volumetric heating that is fast and does not require contact with the polymer tube 10. To heat the tube 10, microwaves may be directed through waveguides or a quasi-optical microwave beam, which is similar to a laser beam, may be used. The emission frequency of the laser beams 18 may vary depending on the particular application and the type of material used to construct the tube 10. In the FIG. 1 example, the system has two lasers 16 and 17. In other implementations, the system may have only one laser or may have additional lasers to provide heat to additional portions of the polymer tube 10.

The laser beams 18 may have a heating area that can range from as small as a micron to as much as a centimeter and may be expanded or reduced in precise amounts throughout the stretching process. By changing the heating area of the laser beams 18, the size of the tube's target portion 22 may be varied during the stretching process. Further control of the stretching process may be provided by changing the heat intensity of the laser beams emitted by the lasers 16 and 17. Increasing the heat intensity of the laser beams 18 will cause greater softening and greater longitudinal stretching of the polymer tube 10, assuming a constant longitudinal force is being applied by the winding system 14. Likewise, lowering the heat intensity of the laser beams 18 will result in less softening and thus less stretching.

The ability to vary the heat intensity of the laser beams 18 may also be used to change the molecular orientation, and thus the physical characteristics, of the polymer tube 10. For example, if the polymer tube 10 is stretched under elevated temperatures (a hot stretch), the stretched tube 10 will have a lower molecular orientation and will be more elastic. If the polymer tube 10 is stretched after little or no heating (a cold stretch), the stretched tube 10 will have a high molecular orientation and will be more stiff.

The winding spool system 14 may include conventional linear motor to control the pulling force applied to the tube 10. In other examples, a clamp, jaw, or other suitable mechanism may be used to create the pulling force on the tube 10. Alternatively, the winding spool could be a pulley system through which the tube 10 is passed and placed in a vertical alignment. A dead weight may then be secured to the tube's leading end 26 to stretch the tube 10. In other implementations, the unwinding spool and motion system 12 may be replaced with another pulling device similar to winding system 14. For example, the unwinding spool may be a linear motor that can feed the polymer tube 10 to the lasers 16 and 17 for heating. In a system where the unwinding system 12 and winding system 14 both include linear motors, the polymer tube 10 may be stretched from either direction, or both directions, by changing the direction and relative speeds of the linear motors. Alternatively, the unwinding and winding systems 12 and 14 could include two clamps to stretch the tube 10. Clamps may be particularly useful when only a small length of polymer tube 10 is being processed by the system, such as a parison for making a balloon.

The controller 36, which is connected to the unwinding system 18, winding system 20, and the lasers 16 and 17, may be used to precisely control the polymer tube's cross-sectional diameter and molecular orientation. The controller 36 may also be used to control the speed of the overall stretching process. For example, by controlling the rate at which the polymer tube 10 is released from the unwinding system 12, it is possible to control the heat intensity and heating area of the lasers 16 and 17, and the speed and longitudinal force applied by the winding system 14. The controller 36 may also cool the heated portion of the tube's leading end 24 with the cooling device 32. The cooling device may be a nozzle that emits super-cooled nitrogen, or another suitable fluid. Alternatively, the cooling device may be a liquid or oil bath through which the leading end 24 of the tube may pass after it is heated and stretched. In other implementations, the cooling device 32 may be omitted.

The controller 36 may further control the stretching process with feedback provided by the temperature sensor 28, the diameter sensor 30, and the tension sensor 34. The temperature sensor 28 may be an infra-red sensor, thermistor, or other suitable type of sensor. Feedback provided to the controller 36 by the temperature sensor may allow the controller 36 to continually adjust the intensity of the heat provided by the lasers 16 and 17. The diameter sensor 30 may measure the cross-sectional diameter of the polymer tube 10 ultrasonically, optically, or some other technique. Feedback may be provided to the controller through the sensor 28 to allow the controller to continually adjust the parameters of the stretching process. The tension sensor may be of a conventional three-roller or on-line sensor. Alternatively, the tension sensor 34 may be a torque sensor that is built into the control systems of most modern motion control systems. For example, in implementations where the winding system 14 is a servo motor, the motor may include a torque sensor that allows the torque of the motor, and thus the longitudinal force applied to the tube 10, to be changed throughout the process. In other implementations, the positions of the sensors 28, 30, and 34 may be changed. Yet in other implementations, the sensors 28, 30, and 34 may be omitted.

Figure 2A:
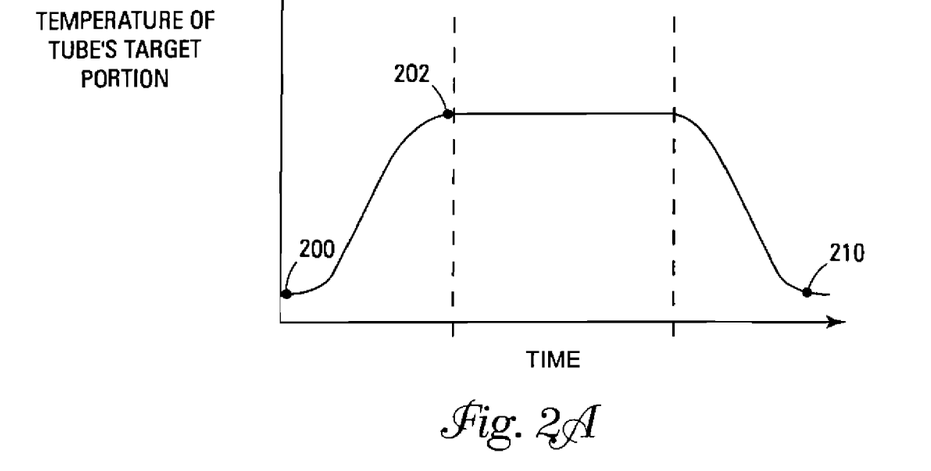
FIGS. 2A and 2B provide an illustration of the heating and stretching of the polymer tube during the process described in FIG. 1.
Figure 2B:
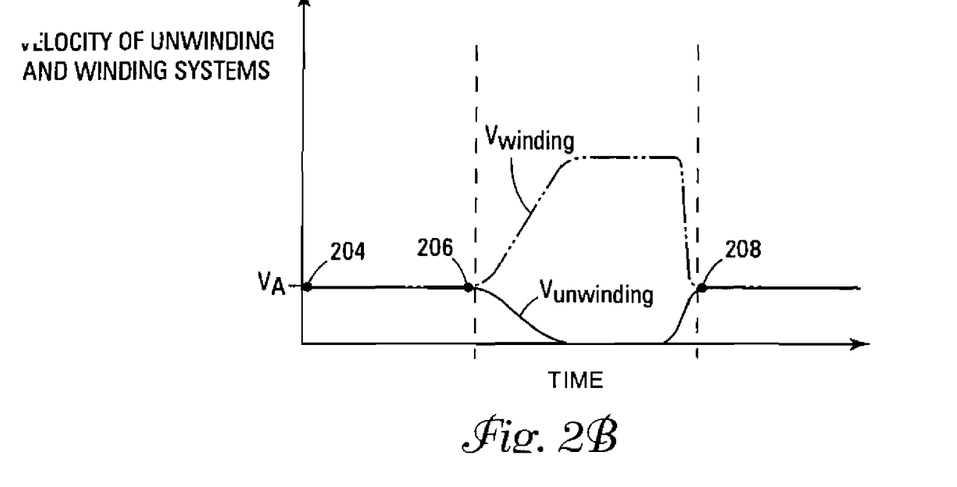

FIGS. 2A and 2B illustrate an exemplary process of heating and stretching a polymer tube using the systems and methods described in FIG. 1. FIGS. 2A and 2B illustrate the coordination of the unwinding system 12, the winding system 14, the lasers 16 and 17, and the cooling device 32 to heat and stretch the polymer tube 10 using the method of FIG. 1. FIG. 2A shows the temperature of the tube's target portion 22 and FIG. 2B shows the velocity at which the unwinding system 12 is providing the tube 20 (Vunwinding) and the winding system 14 is pulling the stretched tube 24 (Vwinding) during the stretching process.

Referring to FIG. 2A, the process begins by using the lasers to apply heat to the target portion of the tube at data point 200 until the target portion is heated to the stretching temperature at data point 202. The stretching temperature is the temperature at which the tube begins to soften and flow. During the heating of the tube's target portion, the unwinding and winding system are operating at the same velocities, as indicated by data points 204 and 206 in FIG. 2B. Thus, during the initial heating of the tube's target portion, there is no tension in the tube and no stretching force is applied. In examples where the lasers' heating area is equal to the area of the tube that will be stretched, the unwinding and winding systems will not be advancing the tube, but rather the tube will be stationary. In examples where the lasers' heating area is smaller than the desired stretching area of the tube, the unwinding and winding systems will be advancing the tube at a specified rate of speed so that the lasers may heat the entire area of the tube that will be stretched.

Once the tube's target portion has been heated to the desired temperature, shown at data point 206, the velocity of the winding system is increased and the velocity of the unwinding system is decreased to apply a longitudinal force to the tube and stretch the tube's target portion. A constant force is applied by the pulling of the winding system using feedback from the tension sensor (shown in FIG. 1). The winding system continues to apply tension to the tube until the tube's target portion is stretched to the desired cross-sectional diameter, as indicated by the diameter sensor (shown in FIG. 1). Once the desired stretching is achieved, the velocity difference between the unwinding and winding systems is reduced, or in some examples eliminated, as indicated by data point 208. The unwinding and winding systems advance the stretched portion of the tube to the cooling device (shown in FIG. 1), which reduces the temperature of the tube's target portion below the stretching temperature, indicated by data point 210 in FIG. 2 A. As the tube is advanced to cool the section that has just been stretched, a new portion of the tube to be stretched is advanced to the laser for heating. The process may then be repeated for the next section of the tube.

As the method is applied to subsequent portions of the tube, the controller may use the feedback provided by the diameter and tension sensors to further fine-tune the stretching process. For example, the diameter sensor may indicate the amount of reduction in the diameter of the tube's target portion based on the amount of tension applied by the winding system. Using the information provided by the amount of tension applied by the winding system may be varied to achieve the precise amount of stretching desired. Alternatively, feedback from the temperature sensor may be used to fine-tune the stretching process. Rather than adjusting the amount of tension applied by the winding system to vary the amount of stretching, the amount of stretching may be increased or decreased by the changing the amount of heat applied by the lasers, and thus, the temperature of the tube's target portion.

In the example of FIGS. 2 A and 2B, the heating and stretching of the polymeric tube are not performed simultaneously. In other words, the target portion of the polymer tube is heated to the desired stretching temperature before the velocity of the winding system is increased to stretch the tube's target portion. In other examples, the target portion of the tube may be simultaneously heated and stretched. In these examples, equilibrium may be achieved between the operational velocities of the winding and unwinding spools and the heat energy provided by lasers. In a state of equilibrium, the lasers apply a constant amount of heat to the tube and the unwinding and winding spools both operate at a constant velocity, with the winding spool velocity being greater than the velocity of the unwinding spool. The difference in velocity creates a constant tension in the tube, and because the heat applied to the tube is constant, the tube is stretched to the same dimension throughout the process.

Equilibrium may be achieved through the use of the controller 36 and the feedback provided by sensors 28, 30, and 34 (shown in FIG. 1). To achieve an optimal result, the controller may be provided with algorithms to automatically execute and optimization method. A quasi-Newtonian non-linear optimization approach, such as the Broyden-Fletcher-Goldfarb-Shanno, is recommended.

FIGS. 3-8 are successive diagrams of an elongate tube, or parison, as it is processed to form a balloon for a balloon catheter. Briefly and by way of overview, the illustrated process includes heating and stretching a first portion of the parison to create a first cone section and a first waist section for the balloon. Next, a second portion of the parison is heated and stretched to form a second cone section and second waist section for the balloon. Between these two heated and stretched portions of the parison is a third portion, which is radially expanded, for example, in a blow-molding chamber, to form a body portion of the balloon.

The process illustrated in FIGS. 3-8 facilitates the manufacture of balloons with high hoop ratios, for example a ratio of 5, that also have hoops strengths suitable for use in cardiac procedures, such as a PTCA. The precise heating and stretching provided by lasers allows a significant reduction in the wall thickness of the cone and waist sections of the parison without a corresponding reduction in the wall thickness of the body section. Because the wall thickness of the body section is maintained during the manufacture of the parison, the parison may be blow molded to large diameters, such as 9 millimeters, without compromising its hoop strength. Moreover, the method permits a reduction in the diameter and wall thickness of the balloon's waist sections to provide greater flexibility and a smaller crossing profile.

Figure 3:
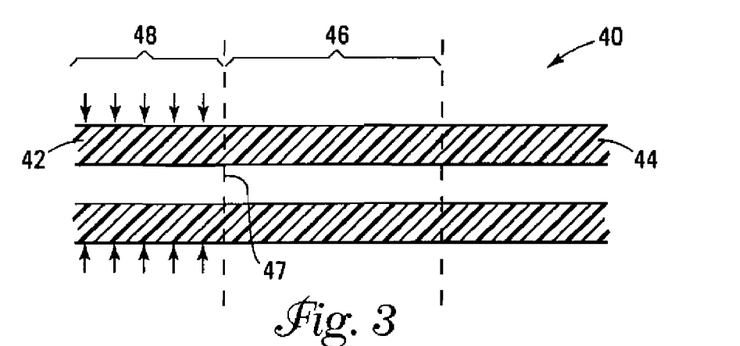
FIGS. 3-8 are successive diagrams of an elongate polymer tube as it is processed to form a balloon for a balloon catheter.

Now, turning to a more detailed description of the process, FIG. 3 shows a cross-sectional view, along a longitudinal plane, of a parison 40 that has a first end 42, a second end 44, and a body section 46 between the first and second ends 40 and 42. A first portion 48 is formed into a first cone section 50 and a first waist section 52 (shown in FIG. 3) by heating the portion 48 with a laser, as indicated by the arrows. The first portion 48 extends from the first end 42 of the parison 40 to an edge 47 of the body section 46 nearest the first end 42. Once the first portion 48 is heated, a pulling force is applied to the first end 42 and stretches the now heated portion 48 of the parison 40 to form the first cone section 50 and the first waist section 52 shown in FIG. 4. The pulling force may be applied by, for example, the winding system 14 shown in FIG. 1 or by some other suitable mechanism.

Figure 4:
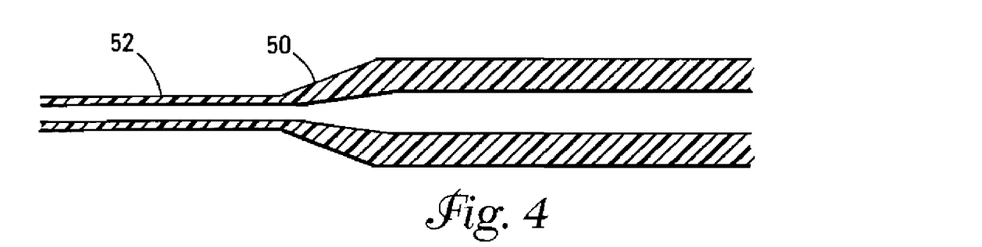

The cone and waist sections 50 and 52 may be formed in a number of different ways using the heating and stretching method of FIG. 1. For example, a laser capable of emitting a laser beam that heats only a small longitudinal section of the first portion 48 may be used to vary the amount of heat applied to the different sections of the first portion 48 during the stretching process. In one example, the first portion 48 is formed by applying heat with a laser to a section of the first portion 48 adjacent to the body portion 46 and moving the laser device, and thus the section of the first portion 48 that is heated, toward the first end 42 while the first portion 48 is stretched by a pulling device at the first end 42. In this example, the cone section 50 is formed by gradually increasing the amount of heat applied by the laser as it moves away from the body portion 46. The gradual increase in heat applied to the first portion 48 causes increased stretching and a corresponding reduction in the diameter of the cone section 50 as shown in FIG. 4. Once the cone section 50 is formed, the level of heat applied by the laser is maintained as the rest of the first portion 48 is stretched to create the waist portion 52.

Figure 5:
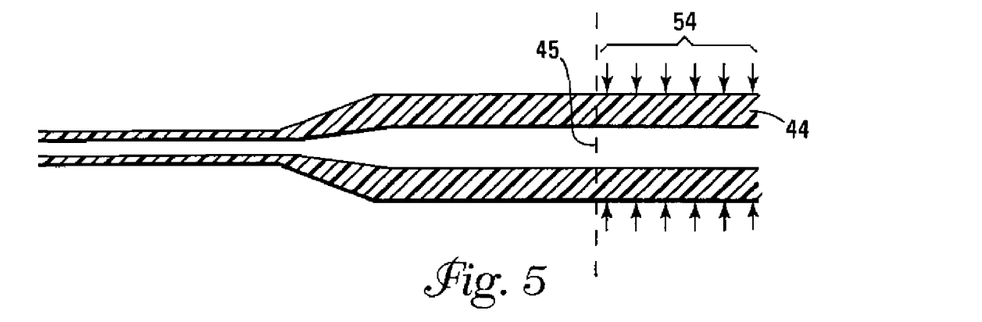
Figure 6:
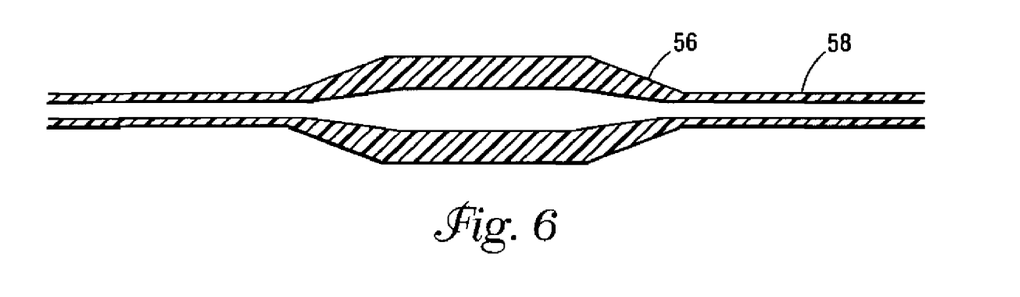

Next, referring to FIG. 5, the second end 44 of the parison 40 is heated and stretched to form a second cone section 56 and second waist section 58 (shown in FIG. 6). The second end 44 is formed by heating a second portion 54 of the parison 40 with a laser as indicated by the arrows. The second portion 54 extends from the second end 44 to an edge 45 of the body section 46 nearest the second end 44. After the portion 54 is heated, a pulling device pulls the second end 44 and stretches the portion 54 of the parison 40 to form the second cone section 56 and the second waist section 58 shown in FIG. 6. The second portion 54 may be heated and stretched in a manner similar to the first portion 48, described previously.

In the example of FIGS. 3-6, the parison 40 was of a uniform length before it was heated and stretched. In other examples, the parison 40 may be pre-processed using a laser ablation or grinding process to remove material in the locations where a thinning of the wall thickness is required. Similarly, laser ablation may be used as a post-processing step to fine-tune the diameter of the parison.

Figure 7:
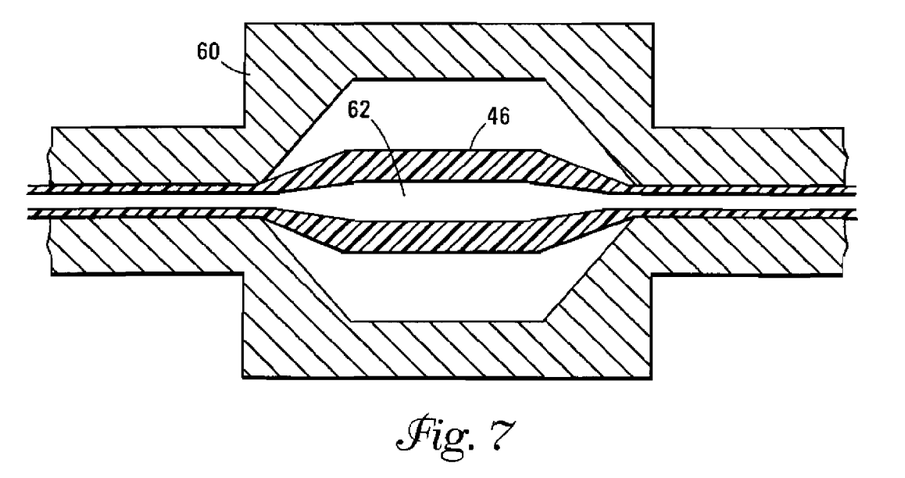
Figure 8:
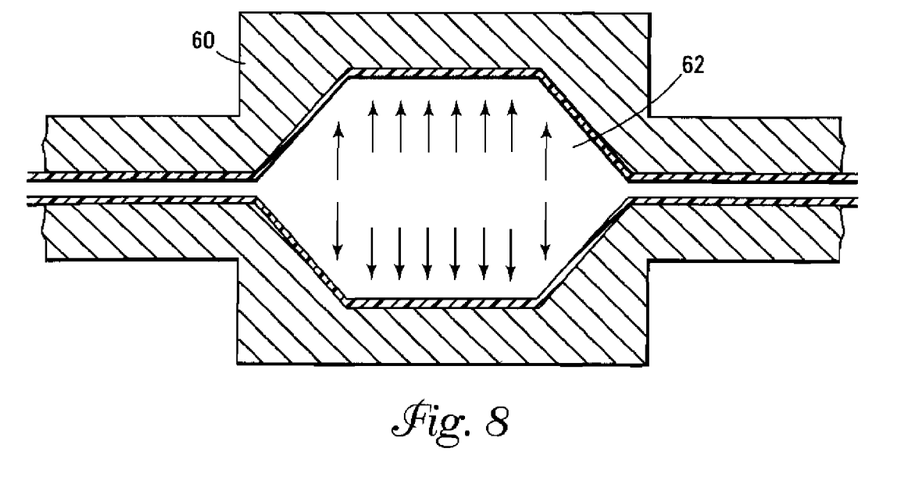

Once the parison 40 is formed to the configuration shown in FIG. 6, the body portion 46 of the parison may be radially expanded to create a balloon. FIGS. 7-8 illustrate the radial expansion of the formed parison 40 in a blow-molding chamber 60. As is conventional in the art, the parison 40 is placed in the chamber 60 as shown in FIG. 7. The chamber 60 is heated to a temperature of 70 to 120 degrees Celsius or more depending upon the parison material and the desired properties of the balloon. Once heated, a pressurized fluid is introduced into an internal chamber 62 of the formed parison 40. The pressure of the fluid causes the parison's body portion 46 to expand as shown in FIG. 8. To achieve expansion of the body section 46 during the blow-mold process, and not just expansion of the cone sections 50 and 56, the chamber 60 may be made out a transparent glass material, such as ZnSe, to allow the body portion 46 to be heated by a laser or microwave. Alternatively, the chamber 60 may be heated to indirectly heat the desired portions of the formed parison 40. For example, the chamber 60 could be divided into a central section that may be heated to heat the body portion 46 and cold sections that cool the cone sections 50 and 56.

Figure 9:
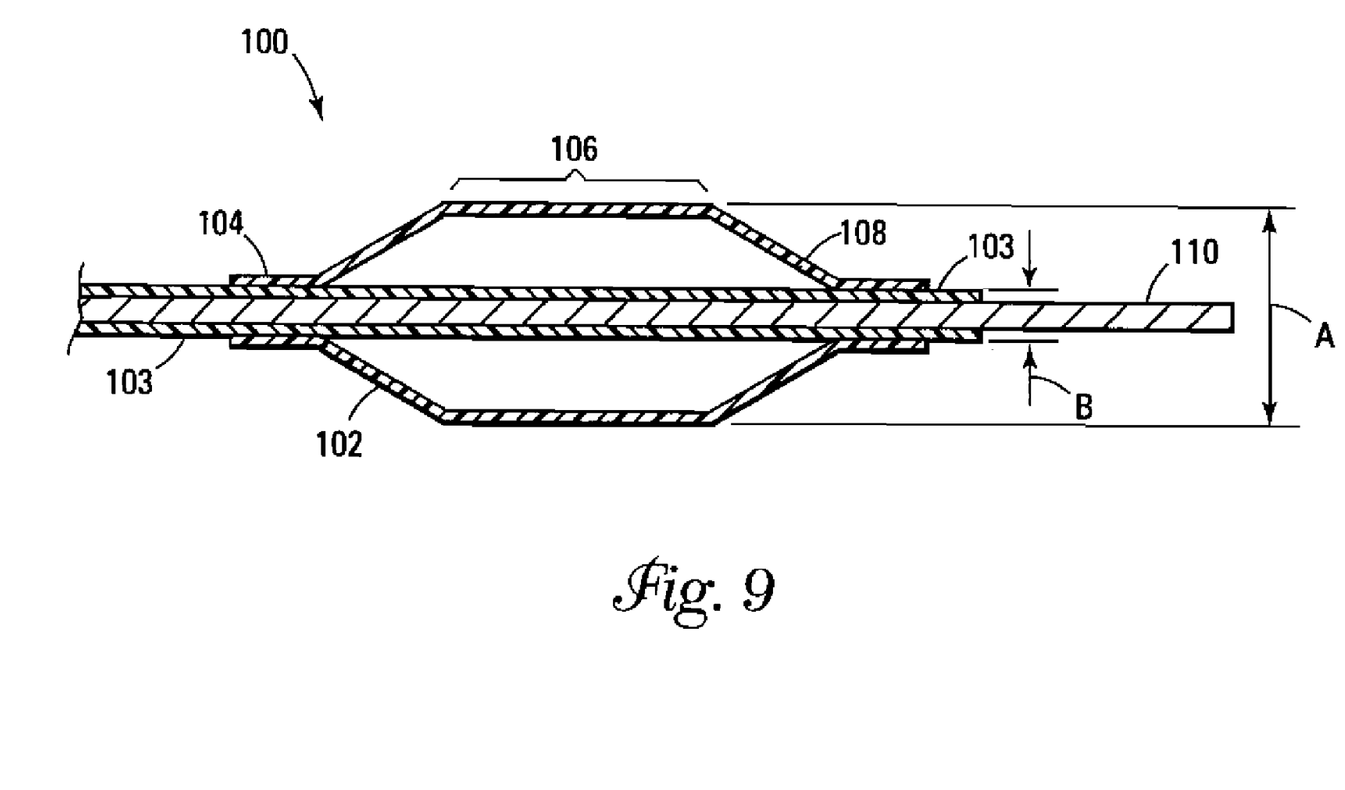
FIG. 9 is a cross-sectional view, along a longitudinal plane, of a distal portion of a balloon catheter that has a balloon manufactured using the system and methods described in FIGS. 1-8.

FIG. 9 is a cross-sectional view, along a longitudinal plane, of a distal portion of a balloon catheter 100 with a balloon 102. The FIG. 9 balloon catheter 100 provides an example of the dimensions of a balloon catheter manufactured using the laser heating and stretching system and methods described in FIGS. 1-8. These methods allow the manufacture of balloons that have an inflated outer diameter greater than about six millimeters for use on a balloon catheter having a 0.014" guide wire, and that are of a suitable hoop strength for use in cardiac procedures and other similar procedures throughout the body.

The catheter 100 includes an elongate shaft 103 that extends through the longitudinal center of the balloon 102. The balloon 102 has a proximal waist section 104, a body portion 106, and a distal waist section 108. A guide wire 110 extends longitudinally through a lumen in the catheter shaft 103 so that the catheter 100 may be guided through vessels in the body. The balloon may be constructed of Nylon 12, PET, PEBAX, PEEK, or a similar material.

In the FIG. 9 example, the balloon catheter's guide wire 110 may have a diameter of 0.014 inches. During a procedure, the guide wire lumen in the catheter's shaft 103 must allow the guide wire 110 to be moved in a longitudinal direction through the lumen; however, the lumen must also be sized appropriately to provide sufficient control of the catheter during a procedure. To achieve these goals, in this example, the inner diameter of the catheter shaft 103 (the guide wire lumen in this example) is slightly larger than the outer diameter of the guide wire so as to appropriately accommodate the guide wire 110 during a procedure. Typically, this requires the inner diameter of lumen through which the guide wire 110 extends to be approximately two thousandths of an inch larger than the outer diameter of the guide wire. In other examples, the diameter of the guide wire 110 and the inner diameter of the catheter shaft 110 may be larger or smaller depending upon the application and the preference of the physician performing the procedure.

In the FIG. 9 example, the balloon 102 may have an inflated diameter of more than 6 millimeters, for example 9 millimeters, as indicated by dimension A. The inflated diameter is the diameter of the body portion 106 of the balloon 102 when it is inflated during a procedure. The balloon also includes waist sections 104 and 108 that are typically welded to the catheter shaft 103 and secure the balloon 102 attaches to the catheter shaft 103 at the balloon's waist sections 104 and 108. The inner waist diameter is the inside diameter of the waist sections 104 and 108 of the balloon 102, and is slightly larger than the outer diameter of the catheter's shaft 103. In this example, the balloon may have an inner waist diameter (indicated by dimension B) that ranges from 0.022 inches, which is typical for a catheter using a 0.014" guide wire, to 0.028 inches. In other examples, the inner diameter may be increased or decreased depending on the size of the catheter shaft 103. In an example where the inflated body portion 106 of the balloon 102 (dimension A) is seven millimeters and the inner waist diameter is 0.022 inches (dimension B), the ratio between these dimensions is approximately 12.5 to 1. In an example where the inflated diameter of the balloon is increased to 9 millimeters, the ratio increases to approximately 16.1 to 1. As the dimensions A and B either increase or decrease in other examples, the ratio between the inflated body portion 106 and the inner waist diameter may vary.

Figure 10:
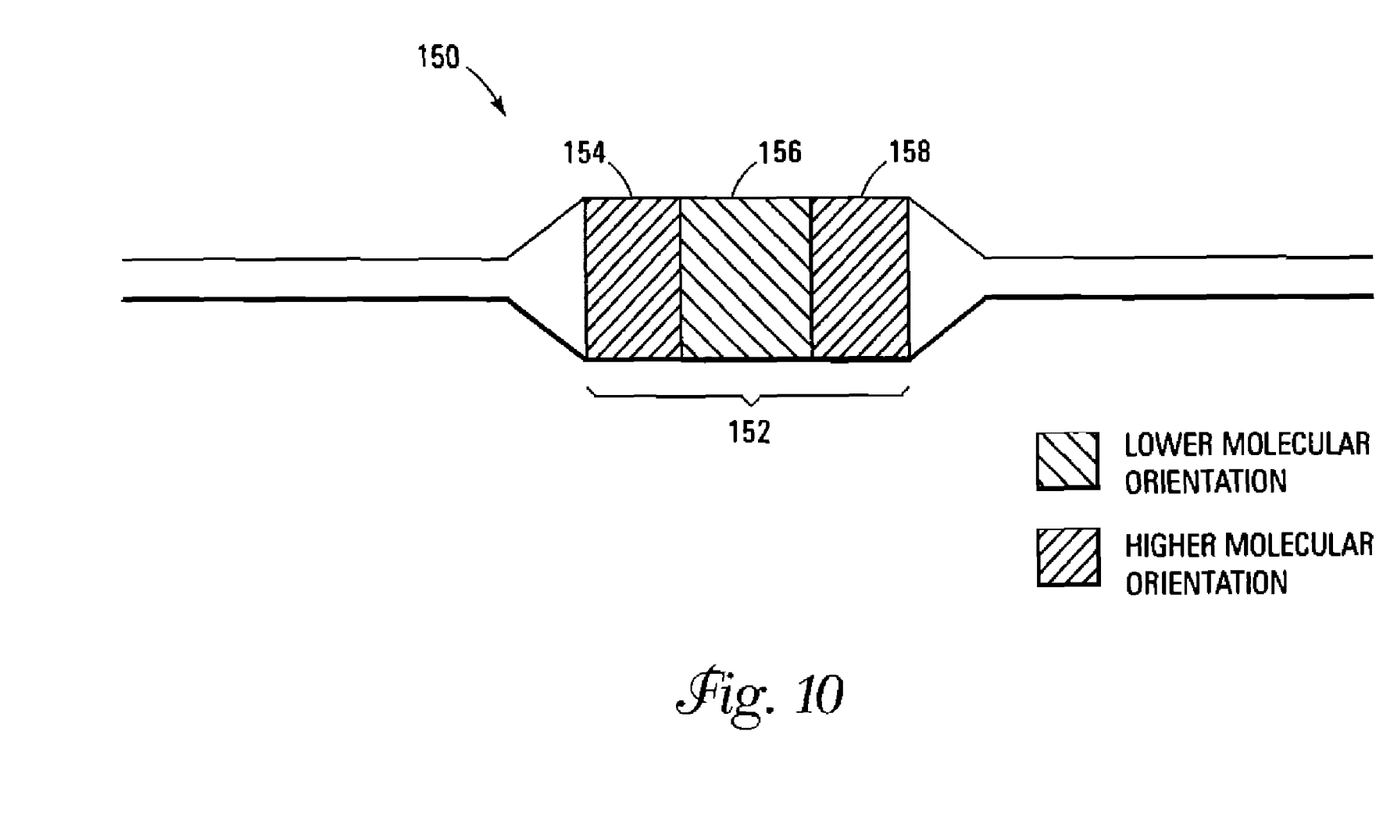
FIG. 10 is a conceptual diagram of a balloon manufactured using the heating and stretching system and methods of FIGS. 1-8, and that illustrates the molecular orientation of polymeric material in a body portion of the balloon.

FIG. 10 is a conceptual diagram of a balloon 150 for a balloon catheter, where the balloon 150 has been manufactured using variations of the heating and stretching processes previously described. In various implementations, the balloon 150 may be made of a single polymeric material, such as PET or PEBAX. The diagram shows a side view of the balloon 150 with markings on the balloon's body portion 152 that illustrate the molecular orientation of three regions 154, 156, and 158 that make up the body portion 152. In this example, the balloon has three regions 154, 156, and 158 that each make up a third of the body portion's length. Using the laser heating and stretching methods, the three regions 154, 156, and 158 may be manufactured with different molecular orientations, and thus different physical characteristics, by varying the amount of heat applied to the regions by the laser during the stretching process. The variation in molecular orientation over this small area, approximately 1-2 centimeters in one example, is possible due to the high level of control over the heating area provided by lasers.

In the FIG. 10 example, the first and third regions 154 and 158 have a high molecular orientation as compared to the second region 156, which is located between the first and third regions 154 and 158. The difference in the orientations of the regions 154, 156, and 158 is accomplished by increasing the heating intensity of the laser device during the stretch of the second region 156 as compared to the heat intensity applied during the stretch of the first and third portions 154 and 158. The increase in heat during the stretching of the second region 156 causes the region 156 to experience a lower molecular orientation, and thus become less compliant than the first and third regions 154 and 158 that were stretched under lower temperatures. Thus, when inflated, the second region 156 may have a greater inflation diameter as compared to the first and third regions 154 and 158. This may be useful in applications such as in various cardiac procedures, in renal procedures, or in other vascular procedures. In other implementations, the body portion 152 may have more or fewer regions than shown in the FIG. 10 example, depending upon the size of the balloon and the desired application.

A number of embodiments of the invention have been described. Nevertheless, it will be understood that various modifications may be made without departing from the spirit and scope of the invention. Accordingly, other embodiments are within the scope of the following claims.

What is claimed is:

1. A method of manufacturing a balloon for a balloon catheter, the method comprising:
   releasing an elongate polymer tube from an unwinding spool at a releasing speed and pulling the polymer tube's leading end by a winding system at a pulling speed;
   heating and longitudinally stretching a first portion of the elongate polymeric tube by a velocity difference between the pulling speed and the releasing speed to form a first reduced diameter portion of the tube that serves as a first waist portion for the balloon;
   heating and longitudinally stretching a second portion of the tube by a velocity difference between the pulling speed and the releasing speed to form a second reduced diameter portion of the tube that serves as a second waist portion for the balloon that is opposite the first end portion, there remaining a body portion located between the first and second end portions;
   expanding the body portion of the tube radially to form the balloon;
   wherein the body portion has a first region;
   laser heating and longitudinally stretching the first region to define a first molecular orientation along the first region;
   wherein the body portion has a second region;
   laser heating and longitudinally stretching the second region to define a second molecular orientation along the second region that is different from the first molecular orientation;
   wherein the body portion has a third region; and
   laser heating and longitudinally stretching the third region to define a third molecular orientation along the third region that is different from the second molecular orientation.

2. The method of claim 1, wherein the heating of the first and second portions is performed by a laser.

3. The method of claim 2, wherein the laser emits a beam in the infrared frequency range to heat the first and second portions.

4. The method of claim 1, wherein before the method is performed the elongate polymeric tube has a uniform diameter.

5. The method of claim 1, wherein the formed balloon has an inflatable body portion with sufficient hoop strength for use in an angioplasty procedure.

6. The method of claim 5, wherein the balloon's inflated outer diameter is more than about 6 millimeters.

7. The method of claim 6, wherein the balloon's inflated outer diameter is about 9 millimeters.

8. The method of claim 1, wherein the first and second waist portions have an inner diameter such that the balloon may be affixed to a catheter shaft that has an inner lumen sized appropriately to accommodate a guide wire having a diameter of at most about 0.055 millimeters.

9. The method of claim 1, wherein the first and second waist portions have an inner diameter of no more than about 0.11 millimeters.

10. The method of claim 1, wherein the formed balloon has an inflatable body portion that has a longitudinal length suitable for use in an angioplasty procedure.

11. The method of claim 1, wherein the formed balloon has an inflatable body portion that has a longitudinal length of no more than about 30 millimeters.

12. The method of claim 1, wherein the second region of the body portion is disposed between the first region and the third region.

13. The method of claim 1, wherein the first molecular orientation is higher than the second molecular orientation.

14. The method of claim 1, wherein the third molecular orientation is higher than the second molecular orientation.

15. The method of claim 1, wherein the first molecular orientation and the third molecular orientation are both higher than the second molecular orientation.

* * * * *